(12) United States Patent
Hruschka et al.

(10) Patent No.: US 9,750,276 B2
(45) Date of Patent: Sep. 5, 2017

(54) METHOD FOR PROCESSING WET OLIVE POMACE

(75) Inventors: Steffen Hruschka, Oelde (DE); Tomas Ignacio Eguiguren Correa, Santiago de Chile (CL); Jose Alberto Corbella, Santiago de Chile (CL)

(73) Assignee: GEA Mechanical Equipment GmbH, Oelde (DE)

( * ) Notice: Subject to any disclaimer, the term of this patent is extended or adjusted under 35 U.S.C. 154(b) by 287 days.

(21) Appl. No.: 14/344,282

(22) PCT Filed: Sep. 11, 2012

(86) PCT No.: PCT/EP2012/067697
§ 371 (c)(1),
(2), (4) Date: Apr. 2, 2015

(87) PCT Pub. No.: WO2013/037751
PCT Pub. Date: Mar. 21, 2013

(65) Prior Publication Data
US 2015/0264970 A1    Sep. 24, 2015

(30) Foreign Application Priority Data
Sep. 12, 2011 (DE) .................. 10 2011 053 527

(51) Int. Cl.
*A23L 3/3454* (2006.01)
*C07B 63/00* (2006.01)
*B30B 9/12* (2006.01)
*A23L 19/00* (2016.01)

(52) U.S. Cl.
CPC ............ *A23L 3/3454* (2013.01); *A23L 19/07* (2016.08); *B30B 9/12* (2013.01); *C07B 63/00* (2013.01)

(58) Field of Classification Search
CPC ......... A23L 3/3454; A23L 19/07; B30B 9/12; C07B 63/00
See application file for complete search history.

(56) References Cited

U.S. PATENT DOCUMENTS

| 3,975,270 A * | 8/1976 | Teranishi .................. A23B 7/10 |
| | | 210/290 |
| 5,094,871 A * | 3/1992 | Heath ...................... A23P 30/20 |
| | | 426/512 |
| 5,928,696 A | 7/1999 | Best et al. |
| 2003/0185921 A1* | 10/2003 | Fotinos ................ G01N 33/505 |
| | | 424/769 |

(Continued)

FOREIGN PATENT DOCUMENTS

| AT | 505026 | * 10/2008 |
| CN | 101781344 | * 7/2010 |

(Continued)

OTHER PUBLICATIONS

English Translation for AT 505026 published Oct. 2008.*

(Continued)

*Primary Examiner* — Anthony Weier
(74) *Attorney, Agent, or Firm* — Crowell & Moring LLP

(57) ABSTRACT

A method for processing wet olive pomace involves providing wet olive pomace, adding a calcium compound and/or a calcium solution to the wet olive pomace, and filtering the wet olive pomace in a first separating device to obtain a solid phase and a liquid phase.

20 Claims, 4 Drawing Sheets

(56) References Cited

U.S. PATENT DOCUMENTS

Figure 1:
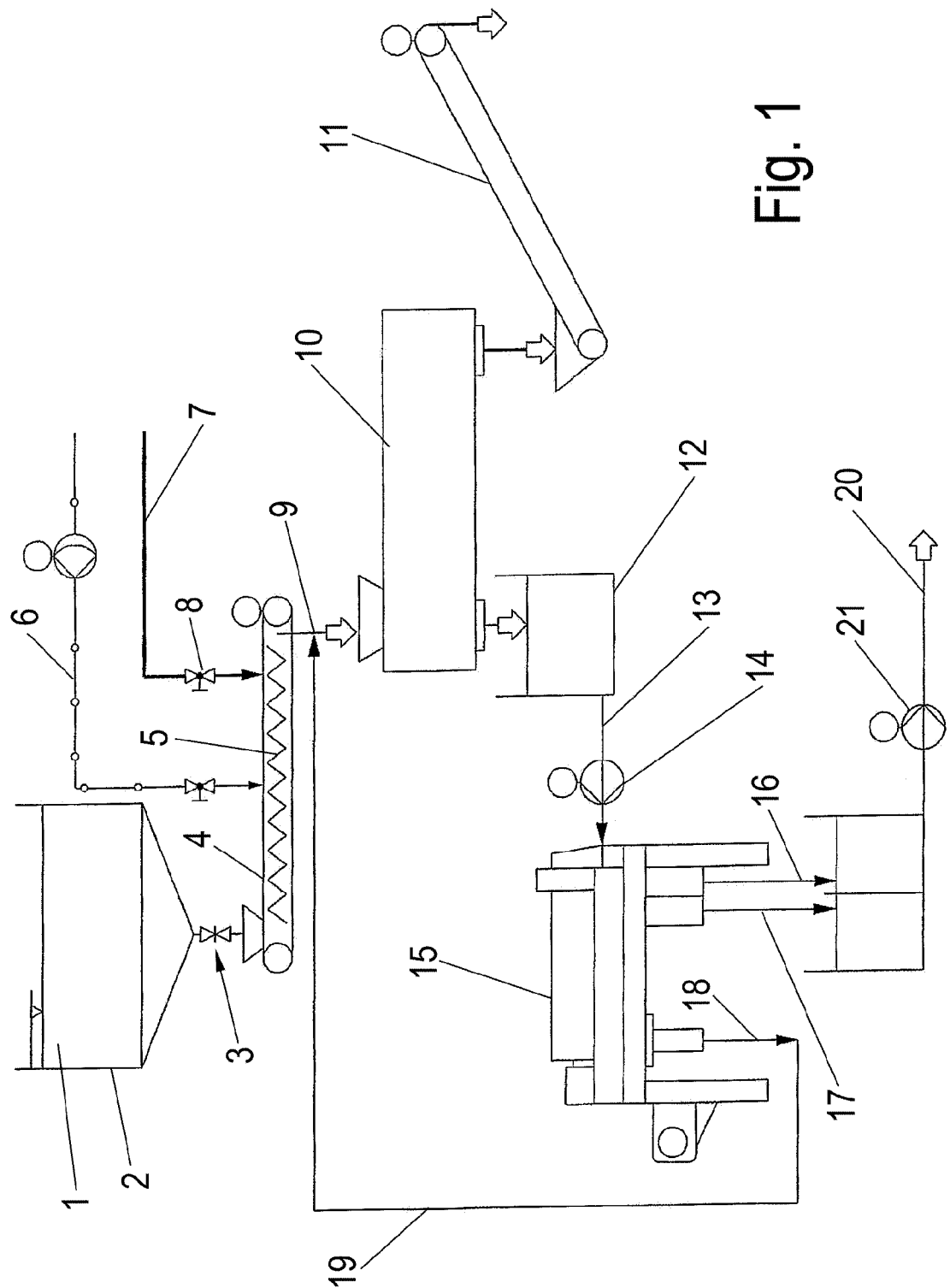

2008/0146828 A1 6/2008 Benavent
2010/0160690 A1* 6/2010 Lopez Mas .............. B01J 19/18
568/810

FOREIGN PATENT DOCUMENTS

| DE | 42 06 006 C1 | | 9/1993 |
|---|---|---|---|
| DE | 195 29 795 C2 | | 2/1996 |
| EP | 0 557 758 A1 | | 9/1993 |
| EP | 0 718 397 A2 | | 6/1996 |
| EP | 1 260 571 A2 | | 11/2002 |
| EP | 1734013 | * | 12/2006 |
| EP | 1810953 | * | 7/2007 |
| WO | WO 2004/110171 A2 | | 12/2004 |
| WO | WO 2005/021695 A1 | | 3/2005 |
| WO | WO 2006/005986 A1 | | 1/2006 |
| WO | WO 2007/042742 A1 | | 4/2007 |
| WO | WO 2007/118920 A1 | | 10/2007 |

OTHER PUBLICATIONS

English Translation for EP1734013 published Dec. 2006.*
English Translation for CN101781344 published Jul. 2010.*
Alburquerque, et al., "Effects of bulking agent on the composting of 'alperujo' the solid by-product of the two-phase centrifugation method for olive oil extraction", Process Biochemistry, vol. 41, No. 1, Jan. 1, 2006, pp. 127-132, Elsevier, NL, XP027983960.
Alburquerque, et al., "Agrochemical characterisation of 'alperujo', a solid by-product of the two-phase centrifugation method for olive oil extraction", Bioresource Technology, vol. 91, No. 2, Jan. 1, 2004, pp. 195-200, XP55042054.
International Preliminary Report on Patentability (PCT/IB/373), including Written Opinion (PCT/ISA/237) dated Mar. 12, 2014 (seven (7) pages).
International Search Report dated Nov. 5, 2012 w/ English translation (six (6) pages).
German Search Report dated May 2, 2012 w/ partial English translation (ten (10) pages).

* cited by examiner

METHOD FOR PROCESSING WET OLIVE POMACE

BACKGROUND AND SUMMARY OF THE INVENTION

Exemplary embodiments of the invention relates to a method for processing wet olive pomace and to a plant for processing wet olive pomace.

German patent document DE 4206006C1 of 16 Sep. 1993 (Düppjohann/Geissen) describes a method in which ground olives are separated in the form of a pulp without the addition of water into the "oil" phase and practically "oil-free pulps". These pulps, which are made up of the two ingredients fruit water (Spanish Alpechin) as well as oil- and water-free pomaces with about 50% moisture (Spanish Orujo), are termed "liquid pomace" or "wet olive pomace".

European patent document EP 1 260 571 A1 discloses a method for extracting oil from fruits or seeds, preferably olives or avocados, with a solid bowl screw-type centrifuge and a plant for the oil extraction. The fruits or seeds are thereby pulverized and during or after pulverization are exposed to high pressure and a subsequent slackening, whereupon the pulverized fruit pulp is supplied to the solid bowl screw-type centrifuge. This separates the incoming pulp into oil and pomace (water/solids mixture) or wet olive pomace ("Alpeorujo").

European patent document EP 0 557 758 A1 discloses a method for extracting olive oil in which a fruit pulp is produced by means of a mill and broken-up in a mixer and then supplied to a solid bowl screw-type centrifuge for the purpose of separating the oil from the fruit pulp. When using fresh olives the production of the fruit pulp can hereby take place without the addition of water, and when using dried olives is carried out with the addition of a slight amount of water according to the state of the olives. The broken-up fruit pulp is separated in a so-called two-phase method more particularly in a two-phase solid bowl screw-type centrifuge into oil and into a solids-water mixture, called "wet olive pomace". The solids-water mixture is suitable for a subsequent extraction and drying process. This procedure is, however, not always desired. This therefore calls for an advantageous further processing of the wet olive pomace.

Further prior art includes European patent document EP 0 718 397 A1; and PCT patent documents WO2007/042742 A1 and WO 2007/118920 A1.

Exemplary embodiments of the present invention are directed to solving this problem. An advantageous method for processing the wet olive pomace is thus to be provided which can be carried out following the or a two-phase method for the oil extraction.

A method according to the invention for processing wet olive pomace comprises at least the following steps: a) providing wet olive pomace; b) adding a calcium compound and/or a calcium solution to the wet olive pomace; and c) filtering the wet olive pomace in a first separating device to obtain a solid phase and a liquid phase.

By adding calcium in the form of the calcium compound more compact solid particles are formed in the wet olive pomace. At the same time, as a result of the more compact structure of the solid particles, less liquid is bonded by the proportion of solids in the wet olive pomace or retained in the wet olive pomace. This released liquid can be mechanically separated so that a processing of the wet olive pomace is also possible so with a view to the end waste disposal and to an economical process management. Through the mechanical separation of the liquid phase from the wet olive pomace the residual moisture content in the liquid-reduced solid phase can be lowered to 50% or less.

The effects of adding a calcium compound lie in a more extensive separation of the liquid or liquor. The solid can be dumped directly as waste. After a phase separation and, where applicable, a further processing even further valuable products (more particularly polyphenols and/or an oil phase) can be obtained from the liquor.

Calcium oxide or lime (foodstuffs additive E529) can advantageously be added to the wet olive pomace as calcium source or compound, or slaked lime (foodstuffs additive E526) can be added as calcium hydroxide and/or wollastonite can be added as calcium (salt solution). Through the shift in the alkali pH value through the addition of these limes, bases or salt solutions or mixtures thereof, polyphenols are also advantageously shifted from the wet olive pomace into the separated liquid phase. These can then be easily isolated from the liquid phase through additional method steps. This optimum extraction of polyphenols makes the method even more economical.

It is moreover advantageous if after preparing the wet olive pomace, according to step a), and preferably prior to adding the calcium compound and/or the calcium solution, according to step b), a mechanical separation of the stones from at least a partial amount of the total amount or from the total amount of wet olive pomace is carried out following an olive oil extraction. These stones can then be dumped or can be used by way of example as fuel (see also FIG. 3). A substantially stone-free wet olive pomace mass of this kind thereby typically has a moisture content of 70-75%, in relation to the total mass of wet olive pomace, and a partially stone-free wet olive pomace mass has a moisture content of 65-70%.

Up until now a mechanical dewatering in the case of such wet sludge could only be carried out up to a residual moisture content of the solid phase of 60-64%. With the method according to the invention it is however possible to carry out a dewatering in a mechanical way wherein the solid phase that is hereby obtained has a residual moisture content of 50%±5%. This remaining solid phase can be dumped as waste, for example.

The amount of added lime to the wet olive pomace should advantageously amount to a maximum of 5%, preferably 2-3%, in relation to the total weight of wet olive pomace, lime or calcium oxide. With a higher addition of lime, liquid is bonded by the lime and cannot be removed from the wet olive pomace through mechanical separation. In order to remove the greatest possible amount of liquid from the wet olive pomace, the proportionate addition of lime of 2-3% has proved particularly expedient.

Starting from the amount of lime added, slaked lime, thus calcium hydroxide, and/or lime water can also be added to the wet olive pomace in a quantity such that it corresponds to the quantity of added lime.

The mechanical separation of a liquid phase from the wet olive pomace by forming a liquid-reduced solid phase can be carried out by a separating device, more particularly in a press.

The processing is preferably carried out before initiating an appreciable fermentation of the product.

A screw press is particularly suitable as a press.

Alternatively a belt press can also be used by way of example as a press.

Alternatively separation can be carried out with a decanter or a filter device.

As a whole the use of a decanter or press has proved particularly advantageous since the proportion of colloidal solids in the separated liquid phase after step c) was comparatively low.

The addition of the calcium oxide and/or the calcium solution can advantageously take place through a dosing unit, preferably as a powder-in-pulp dosing or through the use of a powder dosing machine. The heat that develops during the addition as a result of the exothermic chemical reaction can be controlled by the amount of lime in the dosing unit. A dosing unit furthermore enables a material-saving addition of the corresponding calcium oxide.

The process control can advantageously be carried out by determining and balancing the temperature change in the individual method stages.

A particularly high proportion of liquid phase after the mechanical separation according to step c) could be ascertained when processing fresh wet olive pomace. It is therefore advantageous if the processing of the wet olive pomace from its preparation, according to step a), up to the mechanical separation of the liquid phase from the wet olive pomace by forming the liquid-reduced solid phase, according to step c), is carried out within a maximum of 1 hour, preferably within 30 minutes.

Furthermore a reduction of the residual moisture content could be achieved in the liquid-reduced solid phase by using the wet olive pomace from olives having a degree of ripeness of 4-5, starting from a scale of 1-7, wherein the degree of ripeness 7 indicates the over-ripeness of an olive.

In the case of wet olive pomace obtained from olives with a degree of ripeness of 6-7 or having a standing time before the mechanical separation of the liquid phase, according to step c), of more than 5 h, adding pectin prior to the mechanical separation of the liquid phase, according to step c), has proved expedient in order to separate solids sufficiently from the wet olive pomace.

The liquid phase arising in step c) can be further processed in a further separating device by forming a solid phase, an aqueous phase and where applicable an oil phase. The extraction of polyphenols from the aqueous phase by concentrating the aqueous phase and/or by adsorption has proved particularly advantageous. An additional valuable material can thereby be obtained from a material mixture that hitherto was always rejected as undesired waste. The aqueous phase can be disposed of using a filtration unit.

The residues of the solid phase accumulating during the processing of the liquid phase with a three-phase separation according to step d), can also be recycled in the process. This solid phase need therefore not be stored separately.

According to the invention a plant for processing wet olive pomace comprises at least one mixing device, one dosing unit for the dosed addition of a calcium compound and/or a calcium solution, which opens into the mixing device, and a separating device into which the supply of the wet olive pomace is undertaken from the mixing device and which enables a mechanical separation of a liquid phase by forming a liquid-reduced solid phase.

The dosing unit allows a precise and controlled addition of calcium compound or solution to the wet olive pomace and a uniform distribution of the compound or solution in the wet olive pomace.

BRIEF DESCRIPTION OF THE DRAWING FIGURES

An advantageous variation of the invention will now be explained in further detail with reference to the drawings. These show:

FIGS. 1, 2, 3, and 4 diagrammatic illustrations of different plants according to the invention for carrying out the method according to the invention.

DETAILED DESCRIPTION

FIG. 1 shows an example of a structure of a first plant in which dewatering of the wet olive pomace is carried out.

Wet olive pomace is the name for the pomace residue arising during extraction of olive oil. Wet olive pomace is thereby a phase mixture of, inter alia, water, oil, proteins, pectins, polyphenols, lignins, and other substances.

A pomace residue of this kind is formed when processing olives, in the fresh or dried state in a two-phase separating process in which the olives are separated into olive oil and a water/solids mixture, the latter of which is the wet olive pomace.

FIG. 1 shows a first supply tank 2 for the wet olive pomace 1. The latter is supplied through an outlet valve 3 into a transport and mixing device 4. The mixing device can be by way of example, as shown in FIG. 1, a mixing device 4—here with a screw 5.

In the mixing device 4, a calcium compound, here in particular lime or slaked lime, is added to the pomace by way of example in an aqueous solution, more particularly as limewater. The supply of limewater is through a first supply pipe 7 into the mixing device 4, wherein the supply volume of limewater can be adjusted through a valve 8.

The wet olive pomace that is mixed with lime or slaked lime is transferred from the mixing device 4 at the overflow 9 or through a pipe into a first separating device 10 for separating solids and liquid, for dewatering the wet olive pomace. The dewatering is carried out in the present example in a screw press. Alternatively, other mechanical machines can also be used for dewatering. Preferred machines for dewatering are also, apart from the screw press illustrated in FIG. 1, decanters, belt presses or filters.

The separated solids are discharged from the first separating device 10 (preferably a press, more particularly a screw press, a double-screw press, a centrifugal field separation, more particularly a decanter and/or filter) and sent away via a conveyor belt 11. The discharged solids can then be used by way of example as fuel material.

The separated liquid is transferred to a second supply tank 12. The separated liquid is also termed "liquor". This liquor has a high water content, a proportion of dissolved and suspended solids and a residual oil content.

For optional further processing of the liquor, a second separating device 15—by way of example a three-phase decanter—can be used which removes further residual solids from the liquid and separates the proportion of residual oil from the aqueous phase.

This decanter is connected via a second transfer pipe 13 to the second supply tank 12 so that the liquor can be transferred into the decanter 15 via the second transfer pipe 13 by means of a pump 14.

The solids are discharged from the decanter 15 through the first drainage pipe 18, whilst the oil phase and the water phase are directed from the decanter into corresponding tanks via the second and third drainage pipe 17 (oil phase) and 16 (aqueous phase). The separated solids can be returned to the transfer pipe 9 via a return 19.

The aqueous phase 16 can be discharged from the storage container via a fourth drainage pipe 20 by means of a second pump 21 or can be forwarded to further devices (not shown) for further processing.

Polyphenols can be obtained particularly advantageously from the aqueous phase. For this the aqueous phase is concentrated in a processing method (not shown). This is carried out by evaporation or by CFF (cross-flow filtration). The polyphenol extraction raises the economic efficiency since polyphenols represent a valuable by-product.

The advantageous possibility for polyphenol extraction arises in that the aqueous phase is alkaline (pH value about 12-14) so that the polyphenols exist in the solution separately from the sugars. The polyphenols are hereby particularly easily accessible.

As an alternative or in addition to the concentration of the aqueous phase polyphenols can also be obtained from the aqueous phase by means of adsorbents. Suitable adsorbents are by way of example bentonite, cellulose or the like. The mixing device 4 can optionally comprise an additional supply pipe 6 for introducing pectins.

A variation of a method for dewatering wet olive pomace will now be described in further detail with reference to FIG. 1.

After the formation of the wet olive pomace, stones can be removed from this pomace residue prior to the actual dewatering. Thus, wet olive pomace is supplied to the plant in FIG. 1 directly from the oil extraction process or preferably stone-reduced wet olive pomace is supplied to the plant.

In a third and likewise preferred variation, a mixture of wet olive pomace can also be used in which the stones were previously removed from a part of the mixture and another part of the mixture was discharged directly from the oil extraction process and was subsequently not de-stoned.

The moisture content in the case of untreated or non-stoned wet olive pomace typically amounts to 60-65%. The moisture content of stone-reduced wet olive pomace amounts typically to 70-75%. The moisture content of the mixture from the two types of wet olive pomace typically amounts to between 65-70%.

The wet olive pomace is mixed with the lime or slaked lime after the step of optionally removing the stones. The addition of lime or slaked lime can also take place in the form of limewater. After or at the same time as adding the lime, slaked lime or limewater this is mixed with the wet olive pomace. By adding lime, slaked lime or limewater more compact solids are formed and more liquid is released.

The amount of added lime, thus calcium oxide CaO, advantageously amounts to 2-3% in relation to the weight of the wet olive pomace. The amount of added slaked lime, thus calcium hydroxide $Ca(OH)_2$, is correspondingly higher, between 2.5-4%, in relation to the weight of the wet olive pomace. The amount of the alternatively added limewater should be selected so that the amount of added lime or calcium oxide in the limewater likewise amounts to about 2-3% in relation to the weight of the wet olive pomace.

It is, however, alternatively possible to add a mixture of solid lime or slaked lime and limewater to the wet olive pomace.

A higher amount of lime in the wet olive pomace has a disadvantageous effect since liquid is only released to a reduced extent or the separation of solids and liquid in the wet olive pomace only takes place to a reduced extent and a lower proportion of liquid phase is thereby removed from the wet olive pomace. For this, however, in the case of a higher dosage of lime, preferably in the region between 3-5%, the proportion of colloidal solids in the liquid phase drops from 13% to 8%.

A particularly high proportion of liquid or liquor can be obtained from the stone-free or stone-reduced wet olive pomace. By adding lime it is possible through the subsequent dewatering of the solids to reach a residual moisture content of 50% (±5%). Such partly stoned residues were sludgy and pasty so that a mechanical dewatering of the solids could only arrive at a residual moisture content of about 60-64%.

The addition of lime, slaked lime or limewater and the mixing of the lime, slaked lime or limewater with the wet olive pomace is followed by the phase separation or pressing of the liquid out from the wet olive pomace. This can take place particularly advantageously through a decanter since, with this mechanical separating device for dewatering, the discharged liquid phase has a particularly low proportion of colloidal solids. Alternatively, however, screw presses, belt presses or filter devices can be used.

Optionally, processing of the pressed-out liquor can take place following the aforementioned phase separation or pressing out of the liquid from the wet olive pomace.

For this the liquor is subjected to a further phase separation into a solid phase and an aqueous phase, as well as optionally an oil phase. This phase separation can take place by way of example in a decanter.

The separated solid phase can advantageously be returned to the wet olive pomace prior to the step of dewatering, so that no additional solid phase accumulates as waste.

Should an oil phase accumulate then this can be processed separately.

Polyphenols can be obtained from the aqueous phase and can be used, for example, as fungicides in agriculture.

In a first variation for the additional extraction of polyphenols concentration of the aqueous phase is carried out. This is preferably undertaken by water extraction, by way of example by evaporation or by CFF. The additional extraction of polyphenols can also alternatively take place through adsorption of these substances. Bentonite or cellulose is preferably used as adsorbents. The concentration of the aqueous phase can also advantageously be combined with the adsorption.

A particularly high yield of liquor or pressed-out liquid from the wet olive pomace is produced if the wet olive pomace is fresh, thus is subjected directly following the olive oil extraction to the aforementioned process of dewatering, with or without previous removal of the stones. The dewatering of the wet olive pomace should preferably take place within 5 hours maximum, preferably less than 1 h, preferably however within 30 minutes, after the olive oil extraction. Within the 30 minutes a stable filter cake is produced, which has increasingly lower stability once this time is exceeded.

When lime is added the temperature of the wet olive pomace rises. It has thereby been shown that the control of the dewatering can take place in dependence on the temperature.

Apart from the age of the wet olive pomace, the degree of ripeness of the olives also plays a part in the processing. Particularly good results with a moisture degree of the solid phase after pressing out of less than 50% could be achieved in the case of olives which had a degree of ripeness of 4 to 5 on a scale of 1 to 7, wherein 7 stands for over-ripe olives. When processing very ripe and over-ripe olives it is recommended to additionally add in pectins.

An addition of pectin of 1-2% in relation to the total weight of wet olive pomace is thereby particularly preferred.

By adding the calcium compound, more particularly lime, slaked lime or limewater, the pectins naturally contained in the wet olive pomace mix with calcium compounds and thus form more compact solid compounds. This effect is supported by the use of alkaline Ca-salts for forming compact solids in the wet olive pomace by releasing the liquid.

A particular advantage of the method is seen in the extraction of the polyphenol-rich aqueous phase. The extraction of this product during processing of the wet olive pomace is favored in that the polyphenols during the addition of the alkaline Ca-salts, more particularly when adding lime, slaked lime or limewater, as a result of the change in the pH value, are shifted from the wet olive pomace into the liquor phase or into the liquid phase.

The subsequent processing of the liquor allows the extraction of the polyphenols.

According to FIG. 1 step "b", the addition of a calcium compound and/or a calcium solution to the wet olive pomace, takes place in time "before" step "c", that is before a first, or the, filtering of the wet olive pomace by forming a solid phase and at least one liquid phase in a first separating device.

Figure 2:
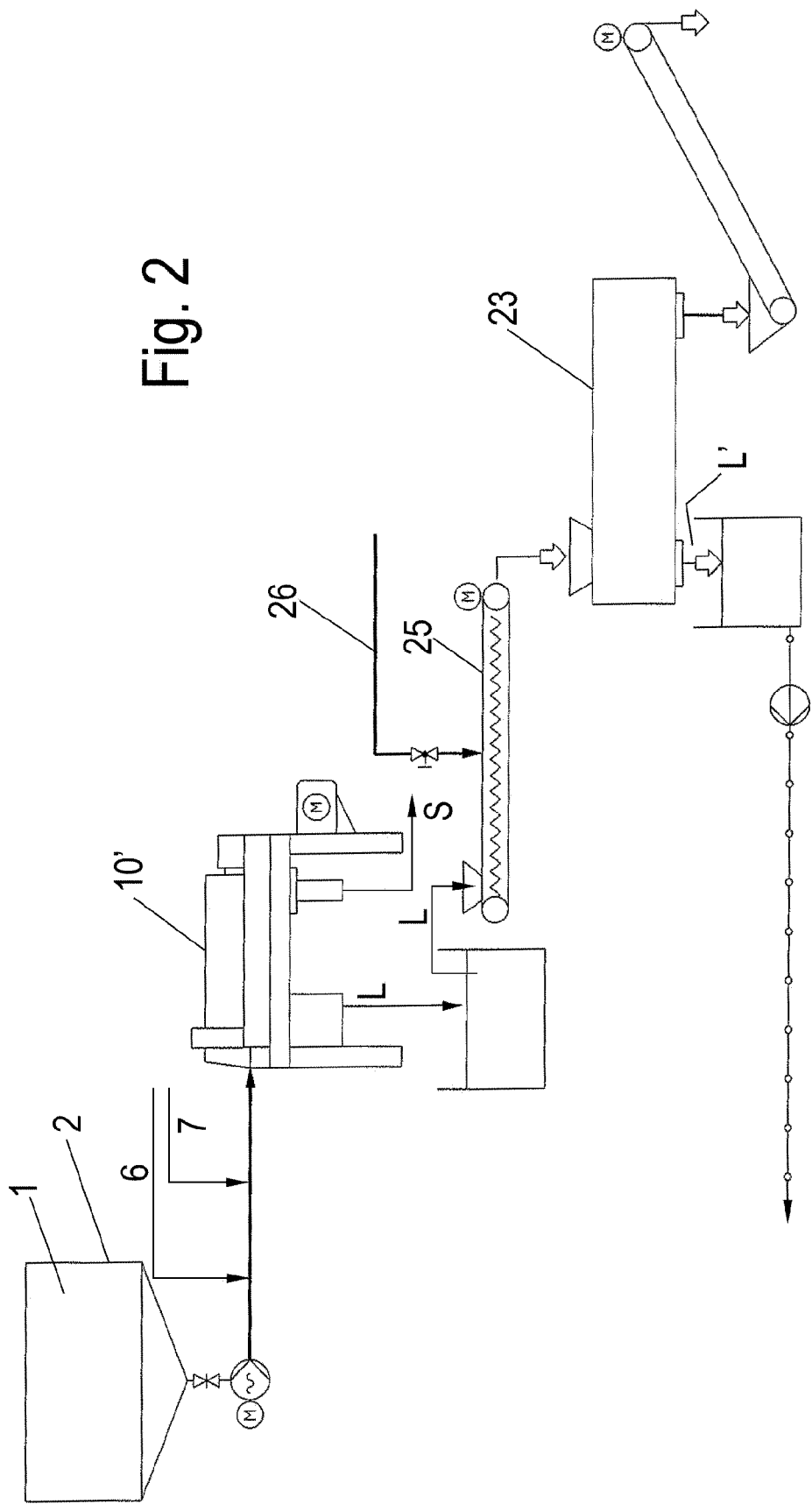

Also according to FIG. 2 step "b" takes place before step "c". However, a decanter 10' is used here as the first separating device 10' for carrying out step "c". A two-phase separation preferably takes place directly into a liquid phase L and a solid phase S. The solid phase S is thereby well dewatered and can be dumped.

The liquid phase L derived from the decanter 10' can optionally be cleaned of further solids S by means of a further separating device 23 (e.g. a press) so that the moisture content in the solid-reduced sludge L' can rise to over 80%. An addition of further substances (e.g. bentonite or flocking agent) can be carried out between the decanter and the further separating device 23, e.g. in a mixture 25 through a pipeline 26.

The liquid phase(s) can be further processed where applicable, by way of example can be separated with a further decanter into an aqueous phase and an oil phase (by way of example in the manner of the processing according to the first separating device 10 in FIG. 1).

Figure 3:
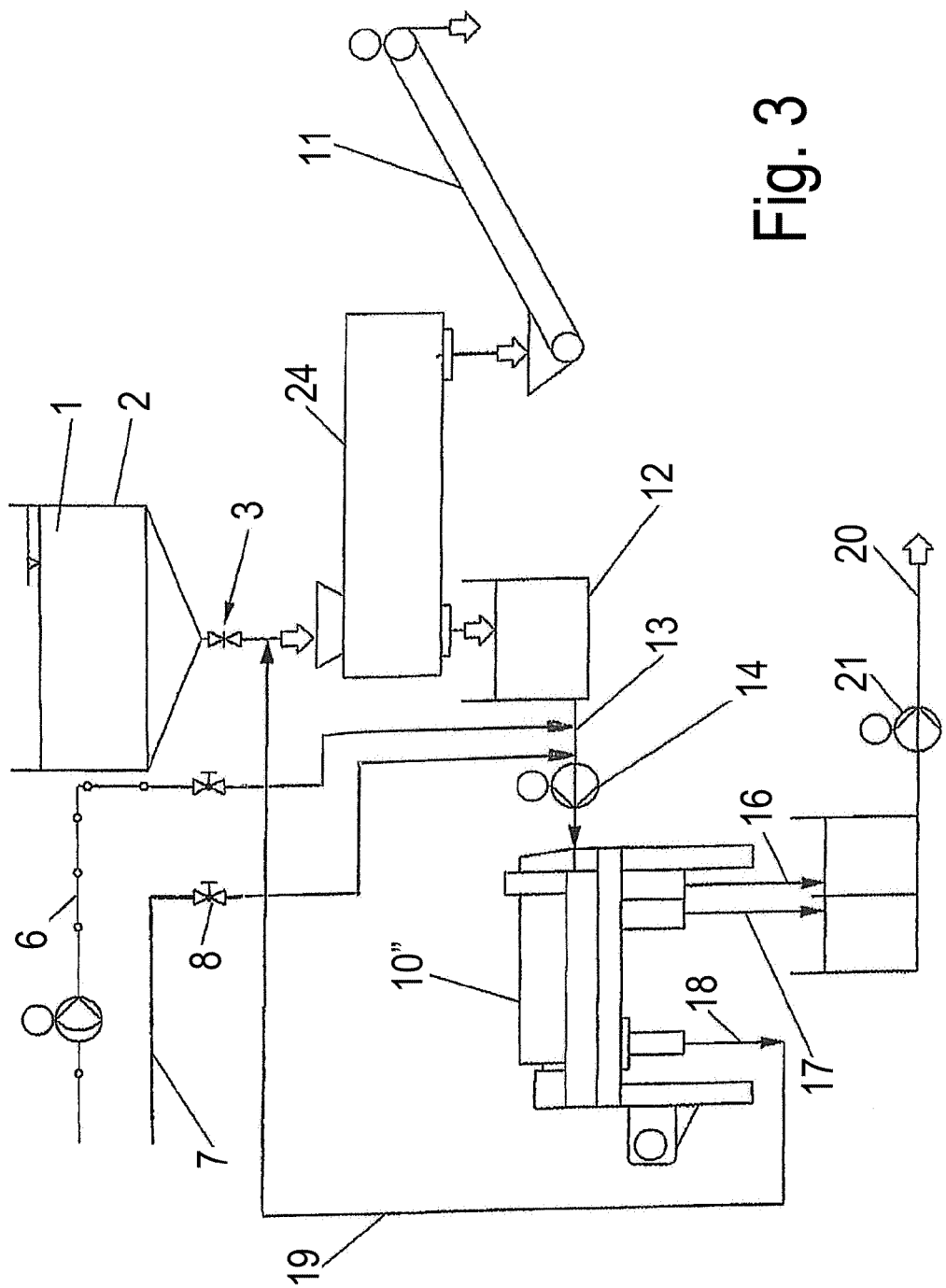

According to FIG. 3 a type of "pre-filtering" of the wet olive pomace to be processed is carried out with a separating device 24'. This first stone—and where applicable further solid phase separation (also skins or the like) is preferably carried out with a press. Also (or in addition) a separation can be carried out essentially only of stones, by way of example with a stone separator (sieve separator; not shown here).

The liquid phase is then further processed for which after the pre-filtering at 7 at least the "lime addition" is carried out. Also here again the optional addition of pectins takes place through the supply pipe 6 after the separation of the stones. Then step "c" is carried out, thus the actual filtering of the pre-filtered wet olive pomace in a separating device 10", which is here a three-phase decanter. Good results are also obtained with this method variation.

Figure 4:
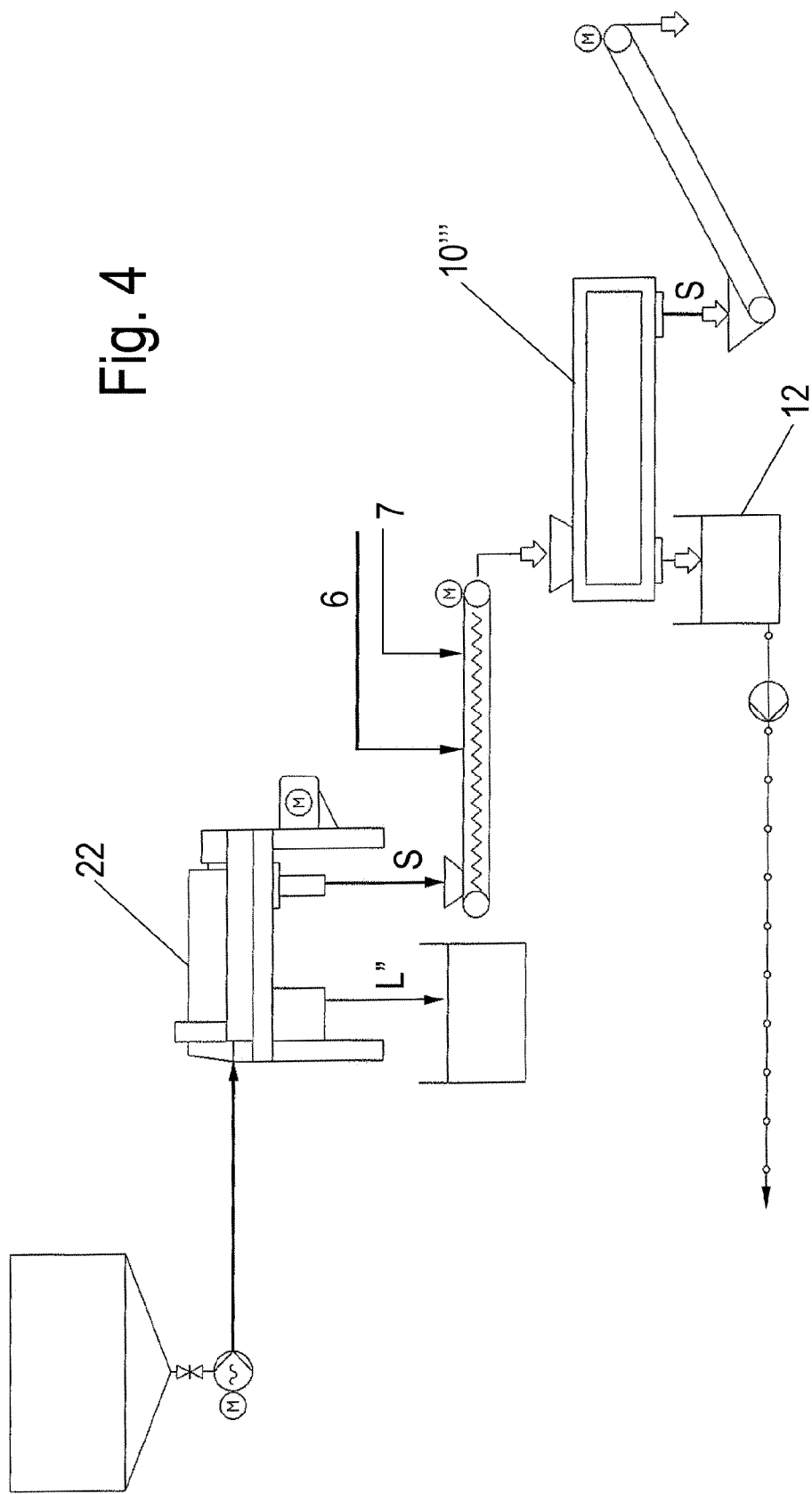

FIG. 4 shows the special case of a preceding oil-water-emulsion separation L" by means of a decanter 22, which can be expedient in individual cases. For this a two-phase decanter can be used. The emulsion is separated in the separating device 22 which is connected in upstream. The still relatively highly fluid "solid phase" S is further separated from solids.

The "lime addition" is then carried out at 6 (and where applicable a pectin addition at 7) into this solid phase S, which is then further dewatered in the separating device 10'''. The further dewatered solid phase S can then be dumped as waste. The liquid phase can where necessary be further processed again, by way of example with a further decanter 15, by way of example corresponding to FIG. 1.

Devices such as dosing valves or pumps or the like (not shown here) can be arranged where necessary in all the pipelines. The foregoing disclosure has been set forth merely to illustrate the invention and is not intended to be limiting.

Since modifications of the disclosed embodiments incorporating the spirit and substance of the invention may occur to persons skilled in the art, the invention should be construed to include everything within the scope of the appended claims and equivalents thereof.

REFERENCE NUMERALS

1 Wet olive pomace
2 Supply tank
3 Outlet valve
4 Mixing device
5 Screw
6 Supply pipe
7 Supply pipe
8 Valve
9 Transfer pipe
10 Separating device (10', 10", 10''')
11 Conveyor belt
12 Supply tank
13 Transfer pipe
14 Pump
15 Separating device
16 Discharge pipe
17 Discharge pipe
18 Discharge pipe
19 Return
20 Discharge pipe
21 Pump
22 Decanter
23 Separating device
24 Separating device
25 Mixer
26 Pipeline

The invention claimed is:

1. A method for processing wet olive pomace, which comprises at least the following steps:
   a) providing wet olive pomace;
   b) adding a calcium compound and/or a calcium solution to the wet olive pomace; and
   c) filtering the wet olive pomace in a first separating device to obtain a liquid-reduced solid phase and at least one liquid phase;
   wherein step b) is carried out before step c) and wherein processing the wet olive pomace from its provision, according to step a), up to mechanical separation of the at least one liquid phase from the wet olive pomace by forming the liquid-reduced solid phase, according to step c), is carried out within a maximum of 1 hour.

2. The method of claim 1, wherein the calcium compound is calcium oxide.

3. The method of claim 1, wherein the calcium compound is calcium hydroxide.

4. The method of claim 1, wherein the calcium compound or the calcium solution is a calcium salt.

5. The method of claim 4, wherein wollastonite is added to the wet olive pomace as the calcium salt.

6. The method of claim 1, wherein after providing the wet olive pomace, according to step a), and before adding the calcium compound and/or the calcium solution, according to step b), a mechanical separation of stones from at least a proportion of a total amount of wet olive pomace is performed following extraction of olive oil.

7. The method of claim 1, wherein after providing the wet olive pomace, according to step a), and before adding the calcium compound and/or calcium solution, according to step b), a mechanical separation of an oil-water emulsion is performed.

8. The method of claim 1, wherein
an amount of between 2-3%, in relation to a total weight of wet olive pomace, of lime is added to the wet olive pomace, or
an amount of slaked lime and/or limewater is added to the wet olive pomace, which amount corresponds to a concentration of calcium in the wet olive pomace when adding an amount of between 2-3% in relation to the total weight of wet olive pomace of lime to the wet olive pomace.

9. The method of claim 1, wherein the filtering according to step c) uses a press as the first separating device.

10. The method of claim 9, wherein the press is a screw press.

11. The method of claim 1, wherein a decanter is the first separating device.

12. The method of claim 1, wherein a filter device is the first separating device.

13. The method of claim 1, wherein the adding of the calcium compound is carried out through a powder-in-pulp dosing unit or by using a powder dosing machine.

14. The method of claim 1, wherein the adding of the calcium solution is carried out by a liquid-liquid dosing unit.

15. The method of claim 1, wherein a process control takes place by determining a temperature of the wet olive pomace, before and/or after adding the calcium compound, according to step b), and/or before and/or after the mechanical separation, according to step c).

16. The method of claim 1, wherein the wet olive pomace is obtained from olives having a degree of ripeness of 4-5, starting from a scale of 1-7, wherein the degree of ripeness 7 indicates the over-ripeness of an olive.

17. The method of claim 1, wherein before step c), pectin is added to the wet olive pomace.

18. The method of claim 1, further comprising the step:
d) processing the at least one liquid phase from step c) in a second separating device by forming a solid phase, an aqueous phase and where applicable an oil phase, wherein the second separating device is a decanter.

19. The method of claim 18, wherein polyphenols are obtained from the aqueous phase.

20. The method of claim 19, wherein the polyphenols are obtained from the aqueous phase by concentrating the aqueous phase and/or by adsorption.

* * * * *